(12) United States Patent
Bykanov et al.

(10) Patent No.: US 10,359,377 B2
(45) Date of Patent: Jul. 23, 2019

(54) BEAM SHAPING SLIT FOR SMALL SPOT SIZE TRANSMISSION SMALL ANGLE X-RAY SCATTEROMETRY

(71) Applicant: KLA-Tencor Corporation, Milpitas, CA (US)

(72) Inventors: Alexander Bykanov, Escondido, CA (US); Nikolay Artemiev, Berkeley, CA (US); Joseph A. Di Regolo, Livermore, CA (US); John Wade Viatella, Pleasant Hill, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 260 days.

(21) Appl. No.: 15/495,634

(22) Filed: Apr. 24, 2017

(65) Prior Publication Data

US 2017/0307548 A1    Oct. 26, 2017

Related U.S. Application Data

(60) Provisional application No. 62/326,648, filed on Apr. 22, 2016.

(51) Int. Cl.
*G21K 1/04* (2006.01)
*G01N 23/201* (2018.01)
*G21K 7/00* (2006.01)

(52) U.S. Cl.
CPC ............ *G01N 23/201* (2013.01); *G21K 1/04* (2013.01); *G21K 7/00* (2013.01);
(Continued)

(58) Field of Classification Search
CPC .......... G01N 23/201; G01N 2223/054; G01N 2223/309; G01N 2223/316; G21K 1/04; G21K 7/00
See application file for complete search history.

(56) References Cited

U.S. PATENT DOCUMENTS 4,535,469 A    8/1985  Brandt
5,608,526 A    3/1997  Piwonka-Corle et al.
(Continued)

FOREIGN PATENT DOCUMENTS

EP    1287342 B1    9/2012
JP    2008-200075 A    9/2008
KR    10-1596749 B1    2/2016

*Primary Examiner* — Courtney D Thomas
(74) *Attorney, Agent, or Firm* — Spano Law Group; Joseph S. Spano

(57) ABSTRACT

Methods and systems for reducing the effect of finite source size on illumination beam spot size for Transmission, Small-Angle X-ray Scatterometry (T-SAXS) measurements are described herein. A beam shaping slit having a slender profile is located in close proximity to the specimen under measurement and does not interfere with wafer stage components over the full range of angles of beam incidence. In one embodiment, four independently actuated beam shaping slits are employed to effectively block a portion of an incoming x-ray beam and generate an output beam having a box shaped illumination cross-section. In one aspect, each of the beam shaping slits is located at a different distance from the specimen in a direction aligned with the beam axis. In another aspect, the beam shaping slits are configured to rotate about the beam axis in coordination with the orientation of the specimen.

20 Claims, 7 Drawing Sheets

(52) U.S. Cl.
CPC . *G01N 2223/054* (2013.01); *G01N 2223/309* (2013.01); *G01N 2223/316* (2013.01)

(56) References Cited

U.S. PATENT DOCUMENTS

| | | | |
|---|---|---|---|
| 5,859,424 A | 1/1999 | Norton et al. | |
| 6,023,338 A | 2/2000 | Bareket | |
| 6,429,943 B1 | 8/2002 | Opsal et al. | |
| 6,716,646 B1 | 4/2004 | Wright et al. | |
| 6,778,275 B2 | 8/2004 | Bowes | |
| 6,787,773 B1 | 9/2004 | Lee | |
| 6,992,764 B1 | 1/2006 | Yang et al. | |
| 7,242,477 B2 | 7/2007 | Mieher et al. | |
| 7,321,426 B1 | 1/2008 | Poslavsky et al. | |
| 7,406,153 B2 | 7/2008 | Berman | |
| 7,478,019 B2 | 1/2009 | Zangooie et al. | |
| 7,626,702 B2 | 12/2009 | Ausschnitt et al. | |
| 7,656,528 B2 | 2/2010 | Abdulhalim et al. | |
| 7,826,071 B2 | 11/2010 | Shchegrov et al. | |
| 7,842,933 B2 | 11/2010 | Shur et al. | |
| 7,873,585 B2 | 1/2011 | Izikson | |
| 7,929,667 B1 | 4/2011 | Zhuang et al. | |
| 7,933,026 B2 | 4/2011 | Opsal et al. | |
| 8,068,662 B2 | 11/2011 | Zhang et al. | |
| 8,138,498 B2 | 3/2012 | Ghinovker | |
| 2003/0021465 A1 | 1/2003 | Adel et al. | |
| 2007/0221842 A1 | 9/2007 | Morokuma et al. | |
| 2009/0152463 A1 | 6/2009 | Toyoda et al. | |
| 2011/0266440 A1 | 11/2011 | Boughorbel et al. | |
| 2012/0292502 A1 | 11/2012 | Langer et al. | |
| 2013/0208279 A1 | 8/2013 | Smith | |
| 2013/0251101 A1* | 9/2013 | Saito | A61B 6/547 378/20 |
| 2013/0304424 A1 | 11/2013 | Bakeman et al. | |
| 2013/0315370 A1 | 11/2013 | Watanabe et al. | |
| 2014/0019097 A1 | 1/2014 | Bakeman et al. | |
| 2014/0111791 A1 | 4/2014 | Manassen et al. | |
| 2014/0172394 A1 | 6/2014 | Kuznetsov et al. | |
| 2014/0222380 A1 | 8/2014 | Kuznetsov et al. | |
| 2014/0297211 A1 | 10/2014 | Pandev et al. | |
| 2015/0110249 A1 | 4/2015 | Bakeman et al. | |
| 2015/0117610 A1 | 4/2015 | Veldman et al. | |
| 2015/0300965 A1 | 10/2015 | Sezginer et al. | |

* cited by examiner

BEAM SHAPING SLIT FOR SMALL SPOT SIZE TRANSMISSION SMALL ANGLE X-RAY SCATTEROMETRY

CROSS REFERENCE TO RELATED APPLICATION

The present application for patent claims priority under 35 U.S.C. § 119 from U.S. provisional patent application Ser. No. 62/326,648, filed Apr. 22, 2016, the subject matter of which is incorporated herein by reference in its entirety.

TECHNICAL FIELD

The described embodiments relate to x-ray metrology systems and methods, and more particularly to methods and systems for improved measurement accuracy.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. A number of metrology based techniques including scatterometry and reflectometry implementations and associated analysis algorithms are commonly used to characterize critical dimensions, film thicknesses, composition and other parameters of nanoscale structures.

Traditionally, scatterometry critical dimension measurements are performed on targets consisting of thin films and/or repeated periodic structures. During device fabrication, these films and periodic structures typically represent the actual device geometry and material structure or an intermediate design. As devices (e.g., logic and memory devices) move toward smaller nanometer-scale dimensions, characterization becomes more difficult. Devices incorporating complex three-dimensional geometry and materials with diverse physical properties contribute to characterization difficulty. For example, modern memory structures are often high-aspect ratio, three-dimensional structures that make it difficult for optical radiation to penetrate to the bottom layers. Optical metrology tools utilizing infrared to visible light can penetrate many layers of translucent materials, but longer wavelengths that provide good depth of penetration do not provide sufficient sensitivity to small anomalies. In addition, the increasing number of parameters required to characterize complex structures (e.g., FinFETs), leads to increasing parameter correlation. As a result, the parameters characterizing the target often cannot be reliably decoupled with available measurements.

In one example, longer wavelengths (e.g. near infrared) have been employed in an attempt to overcome penetration issues for 3D FLASH devices that utilize polysilicon as one of the alternating materials in the stack. However, the mirror like structure of 3D FLASH intrinsically causes decreasing light intensity as the illumination propagates deeper into the film stack. This causes sensitivity loss and correlation issues at depth. In this scenario, SCD is only able to successfully extract a reduced set of metrology dimensions with high sensitivity and low correlation.

In another example, opaque, high-k materials are increasingly employed in modern semiconductor structures. Optical radiation is often unable to penetrate layers constructed of these materials. As a result, measurements with thin-film scatterometry tools such as ellipsometers or reflectometers are becoming increasingly challenging.

In response to these challenges, more complex optical metrology tools have been developed. For example, tools with multiple angles of illumination, shorter illumination wavelengths, broader ranges of illumination wavelengths, and more complete information acquisition from reflected signals (e.g., measuring multiple Mueller matrix elements in addition to the more conventional reflectivity or ellipsometric signals) have been developed. However, these approaches have not reliably overcome fundamental challenges associated with measurement of many advanced targets (e.g., complex 3D structures, structures smaller than 10 nm, structures employing opaque materials) and measurement applications (e.g., line edge roughness and line width roughness measurements).

Atomic force microscopes (AFM) and scanning-tunneling microscopes (STM) are able to achieve atomic resolution, but they can only probe the surface of the specimen. In addition, AFM and STM microscopes require long scanning times. Scanning electron microscopes (SEM) achieve intermediate resolution levels, but are unable to penetrate structures to sufficient depth. Thus, high-aspect ratio holes are not characterized well. In addition, the required charging of the specimen has an adverse effect on imaging performance. X-ray reflectometers also suffer from penetration issues that limit their effectiveness when measuring high aspect ratio structures.

To overcome penetration depth issues, traditional imaging techniques such as TEM, SEM etc., are employed with destructive sample preparation techniques such as focused ion beam (FIB) machining, ion milling, blanket or selective etching, etc. For example, transmission electron microscopes (TEM) achieve high resolution levels and are able to probe arbitrary depths, but TEM requires destructive sectioning of the specimen. Several iterations of material removal and measurement generally provide the information required to measure the critical metrology parameters throughout a three dimensional structure. But, these techniques require sample destruction and lengthy process times. The complexity and time to complete these types of measurements introduces large inaccuracies due to drift of etching and metrology steps. In addition, these techniques require numerous iterations which introduce registration errors.

Transmission, Small-Angle X-Ray Scatterometry (T-SAXS) systems have shown promise to address challenging measurement applications. Current T-SAXS tools employ a beam forming slits to form the illumination beam incident on the specimen under measurement. A beam divergence shaping slit is located in the beam path before or after the focusing optics to define the divergence angle of the beam. A beam shaping slit is located in the beam path after the beam divergence shaping slit to define the size of the beam spot incident on the wafer.

Unfortunately, available x-ray sources have a finite dimension in directions orthogonal to the direction of beam propagation. Due to finite source size, the beam spot incident on the specimen will be defined by the size of the beam shaping slit and the angular dimension of the source from the optics (e.g., focusing optics, collimating optics, etc.). For example, the size of the image of an x-ray source in a focal plane of an optical system is defined by its actual size and the magnification of the optics. The magnification of the optics is the ratio of the distance from the focusing optic to the image and the distance from the focusing optic to the source. In addition, slope and figure errors of the focusing optics will further increase the beam spot size. Current systems do not meet the requirements for measurements of metrology targets located in scribe lines where a beam spot size of 50 micrometers, or less, is required.

To address this problem, it is possible to reduce the size of the beam shaping slit. However, this results in a dramatic reduction of photon flux, which makes renders the measurements ineffective. Furthermore, reducing the size of the beam shaping slit does not completely solve the problem because beam divergence always contributes to beam spread at the point of incidence with the specimen under measurement. For example, in typical T-SAXS systems the beam shaping slit is more than 250 millimeters from the surface of specimen under measurement. For typical beam divergence present in these systems, a beam spot size of 30-40 micrometers is expected even if the size of the beam shaping slit were infinitesimally small. Of course, this arrangement is impractical because an infinitesimally small amount of illumination would be projected onto the specimen if a measurement system were configured in such a manner.

The impact of beam divergence on beam spot size can be reduced by locating the beam shaping slit closer to the specimen. However, in current practice, this has not been achieved for T-SAXS systems. An effective T-SAXS metrology system performs measurements of a specimen oriented at different angles of incidence with respect to the incoming beam. In other words, the specimen is tilted with respect to the incoming beam such that a surface normal of the specimen is oriented from the beam axis of the illumination beam by as much as 30 degrees, or more. Under these conditions, traditional beam shaping slits mechanically interfere with the specimen if they are not spaced apart from the specimen by a significant distance. In current systems implemented by KLA-Tencor Corporation, the distance between the beam shaping slit and the specimen under measurement is 260 millimeters.

U.S. Pat. No. 7,406,153 describes a grazing incidence tool which employs knife edge beam blocks in close proximity to the specimen under measurement. However, the disclosed beam blocks are only functional in the context of a grazing incidence tool, not a T-SAXS tool where normal illumination, or illumination at angles up to 50 degrees from normal are required.

To further improve device performance, the semiconductor industry continues to focus on vertical integration, rather than lateral scaling. Thus, accurate measurement of complex, fully three dimensional structures is crucial to ensure viability and continued scaling improvements. Future metrology applications present challenges for metrology due to increasingly small resolution requirements, multi-parameter correlation, increasingly complex geometric structures including high aspect ratio structures, and increasing use of opaque materials. Thus, methods and systems for improved T-SAXS measurements are desired.

SUMMARY

Methods and systems for reducing the effect of finite source size on illumination beam spot size for Transmission, Small-Angle X-ray Scatterometry (T-SAXS) measurements are described herein.

In one aspect, a beam shaping slit is located in close proximity to the specimen under measurement. The beam shaping slit has a slender profile that does not interfere with wafer stage components even at large angles of incidence (e.g., angles of incidence up to 60 degrees) of the T-SAXS measurement system. By locating the beam shaping slit in close proximity to the specimen, the effect of beam divergence on beam spot size is minimized. In addition, beam placement accuracy on a metrology target is improved because the beam profile of the incident beam spot is sharply defined with minimal shadow zones at the edges.

In some embodiments, a beam shaping slit mechanism includes multiple, independently actuated beam shaping slits. In one embodiment, four independently actuated beam shaping slits are employed to effectively block a portion of an incoming x-ray beam and generate an output beam having a box shaped illumination cross-section.

In a further aspect, each of the slits of a beam shaping slit mechanism are located at different distances from the surface of specimen along the beam axis. In this manner, the slits spatially overlap as viewed along the beam axis without mechanical interference.

In another further aspect, a beam shaping slit mechanism is configured to rotate about the beam axis in coordination with the orientation of the specimen to optimize the profile of the incident beam for each angle of incidence, azimuth angle, or both. In this manner, the beam shape is matched to the shape of the metrology target.

In another aspect, the measurement quality and performance of a T-SAXS system is estimated based on properties of the measured zero order beam. The measured properties of the zero order beam include, but are not limited to beam shape, intensity, location, profile, tilt, rotation, asymmetry, or any combination thereof.

In a further aspect, the measurement quality and performance of the metrology system is controlled based on the measured zero order beam. In some examples, the estimates of measurement quality and performance described hereinbefore are provided as input to a feedback controller. The feedback controller communicates control commands that result in changes in state of one or more elements of the metrology system that improves measurement system quality and performance.

In another further aspect, a metrology system is configured to generate a structural model (e.g., geometric model, material model, or combined geometric and material model) of a measured structure of a specimen, generate a T-SAXS response model that includes at least one geometric parameter from the structural model, and resolve at least one specimen parameter value by performing a fitting analysis of measurement data with the response model. In this manner, a comparison of simulated T-SAXS signals with measured data enables the determination of geometric as well as material properties such as electron density and elemental identification and composition of the sample.

In a further aspect, an initial estimate of values of one or more parameters of interest is determined based on T-SAXS measurements performed at a single orientation of the incident x-ray beam with respect to the measurement target. The initial, estimated values are implemented as the starting values of the parameters of interest for a regression of the measurement model with measurement data collected from measurements at multiple orientations. In this manner, a close estimate of a parameter of interest is determined with a relatively small amount of computational effort, and by implementing this close estimate as the starting point for a regression over a much larger data set, a refined estimate of the parameter of interest is obtained with less overall computational effort.

In a further aspect, T-SAXS measurement data is used to generate an image of a measured structure based on the measured intensities of the detected diffraction orders. In some embodiments, a response function model is generalized to describe the scattering from a generic electron density mesh. Matching this model to the measured signals, while constraining the modelled electron densities in this mesh to enforce continuity and sparse edges, provides a three dimensional image of the sample.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for reducing the effect of beam divergence defined by finite source size on illumination beam spot size for Transmission, Small-Angle X-ray Scatterometry (T-SAXS) measurements are described herein.

Practical T-SAXS measurements in a semiconductor manufacturing environment require measurements over a large range of angles of incidence with respect to the surface of a specimen (e.g., semiconductor wafer) and small beam spot size (e.g., less than 50 micrometers across the effective illumination spot).

In one aspect, a beam shaping slit is located in close proximity to the specimen under measurement (i.e., less than 100 millimeters). The beam shaping slit has a slender profile that does not interfere with wafer stage components over the full operating range of angles of incidence of the T-SAXS measurement system (e.g., angles of incidence up to 60 degrees). By locating the beam shaping slit in close proximity to the specimen, the effect of beam divergence on beam spot size is minimized. In addition, beam placement accuracy on a metrology target is improved because the beam profile of the incident beam spot is sharply defined with minimal shadow zones at the edges.

In some embodiments, the metrology target characterized by T-SAXS measurements as described herein is located within a scribe line of the wafer under measurement. In these embodiments, the metrology target is sized to fit within the width of the scribe line. In some examples, the scribe line width is less than eighty micrometers. In some examples, the scribe line is less than fifty micrometers. In general, the width of the scribe lines employed in semiconductor manufacturing is trending smaller.

In some embodiments, the metrology target characterized T-SAXS measurements as described herein is located within an active die area of the wafer under measurement and is a part of a functional integrated circuit (e.g., memory, image sensor, logic device, etc.).

In general, it is preferred that the illumination beam spot size closely match the lateral dimensions of the metrology target under measurement to minimize contamination signals from structures surrounding the metrology target under measurement. In some embodiments, the metrology target under measurement is less than 50 micrometers in any lateral dimension. In some embodiments, the metrology target under measurement is less than 30 micrometers in any lateral dimension. In some embodiments, the beam spot size is less than 50 micrometers. In some embodiments, the beam spot size is less than 30 nanometers. This enables controlled illumination of a metrology target located within a scribe line.

Figure 1:
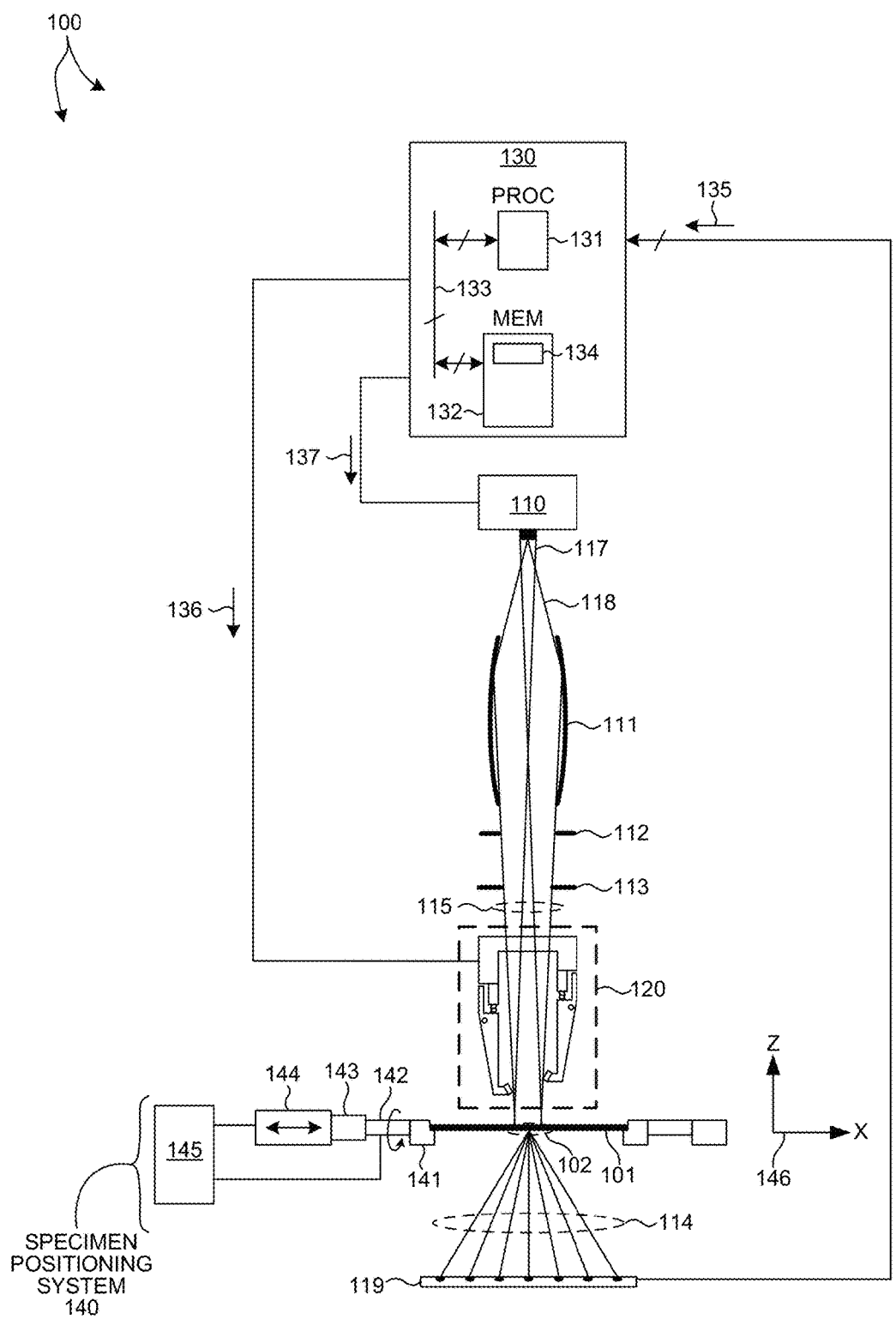
FIG. 1 is a diagram illustrative of a metrology system 100 configured to perform T-SAXS measurements with beam shaping slits in close proximity to the specimen under measurement in accordance with the methods described herein.

FIG. 1 illustrates an embodiment of a T-SAXS metrology tool 100 for measuring characteristics of a specimen in accordance with the exemplary methods presented herein. As shown in FIG. 1, the system 100 may be used to perform T-SAXS measurements over an inspection area 102 of a specimen 101 illuminated by an illumination beam spot.

In the depicted embodiment, metrology tool 100 includes an x-ray illumination source 110 configured to generate x-ray radiation suitable for T-SAXS measurements. In some embodiments, the x-ray illumination system 110 is configured to generate wavelengths between 0.01 nanometers and 1 nanometer. In general, any suitable high-brightness x-ray illumination source capable of generating high brightness x-rays at flux levels sufficient to enable high-throughput, inline metrology may be contemplated to supply x-ray illumination for T-SAXS measurements. In some embodiments, an x-ray source includes a tunable monochromator that enables the x-ray source to deliver x-ray radiation at different, selectable wavelengths.

In some embodiments, one or more x-ray sources emitting radiation with photon energy greater than 15 keV are employed to ensure that the x-ray source supplies light at wavelengths that allow sufficient transmission through the entire device as well as the wafer substrate. By way of non-limiting example, any of a particle accelerator source, a liquid anode source, a rotating anode source, a stationary, solid anode source, a microfocus source, a microfocus rotating anode source, and an inverse Compton source may be employed as x-ray source 110. In one example, an inverse Compton source available from Lyncean Technologies, Inc., Palo Alto, Calif. (USA) may be contemplated. Inverse Compton sources have an additional advantage of being able to produce x-rays over a range of photon energies, thereby enabling the x-ray source to deliver x-ray radiation at different, selectable wavelengths.

Exemplary x-ray sources include electron beam sources configured to bombard solid or liquid targets to stimulate x-ray radiation. Methods and systems for generating high brightness, liquid metal x-ray illumination are described in U.S. Pat. No. 7,929,667, issued on Apr. 19, 2011, to KLA-Tencor Corp., the entirety of which is incorporated herein by reference.

X-ray illumination source 110 produces x-ray emission over a source area having finite lateral dimensions (i.e., non-zero dimensions orthogonal to the beam axis. Focusing optics 111 focuses source radiation onto a target. The finite lateral source dimension results in finite spot size 102 on the target 101 defined by the rays 117 coming from the edges of the source. In some embodiments, focusing optics 111 includes elliptically shaped focusing optical elements.

A beam divergence control slit 112 is located in the beam path between focusing optics 111 and beam shaping slit mechanism 120. Beam divergence control slit 112 limits the divergence of the illumination provided to the specimen under measurement. An additional intermediate slit 113 is located in the beam path between beam divergence control slit 112 and beam shaping slit mechanism 120. Intermediate slit 113 provides additional beam shaping. In general, however, intermediate slit 113 is optional.

Beam shaping slit mechanism 120 is located in the beam path immediately before specimen 101. In one aspect, the slits of beam shaping slit mechanism 120 are located in close proximity to specimen 101 to minimize the enlargement of the incident beam spot size due to beam divergence defined by finite source size. In some embodiments, the slits of beam shaping slit mechanism 120 are located within 50 millimeters of the location of beam incidence with specimen 101. In some embodiments, the slits of beam shaping slit mechanism 120 are located within 30 millimeters of the location of beam incidence with specimen 101. In some embodiments, the slits of beam shaping slit mechanism 120 are located within 10 millimeters of the location of beam incidence with specimen 101. In one example, expansion of the beam spot size due to shadow created by finite source size is approximately one micrometer for a 10 micrometer x-ray source size and a distance of 25 millimeters between the beam shaping slits and specimen 101.

Figure 2:
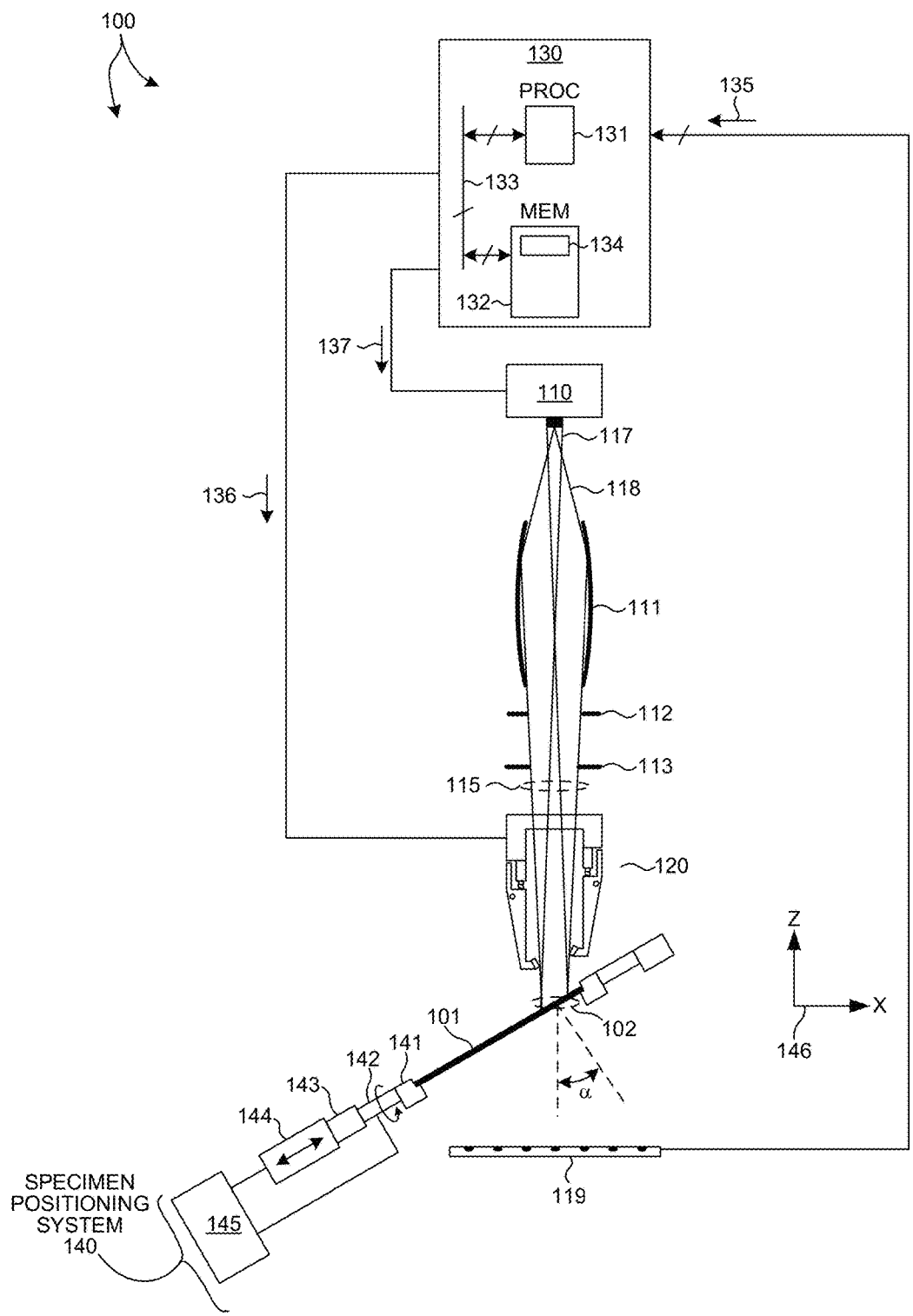
FIG. 2 is a diagram illustrative of metrology system 100 depicted in FIG. 1 with the specimen oriented with respect to the incident beam of x-ray radiation at a large incidence angle.

The beam shaping slit mechanism 120 is shaped such that there is no mechanical interference with specimen positioning system 140 when specimen 101 is oriented over a broad range of angles of incidence. In some embodiments, the illumination beam is provided to the surface of specimen 101 at an angle of incidence that varies as much as 60 degrees from normal incidence. FIG. 2 depicts T-SAXS system 100 when specimen positioning system 140 positions specimen 101 at a non-normal angle of incidence with respect to the beam of incident illumination light. For purposes of illustration, the light scattered from specimen 101 is not illustrated in FIG. 2. As illustrated in FIG. 2, a surface normal of specimen 101 is oriented at an angle, α, with respect to the beam axis of the incident illumination light. In some embodiments, beam shaping slit mechanism 120 is shaped such that there is no mechanical interference with specimen positioning system 140 when specimen 101 is oriented at an angle, α, of 20 degrees, or more. In some embodiments, beam shaping slit mechanism 120 is shaped such that there is no mechanical interference with specimen positioning system 140 when specimen 101 is oriented at an angle, α, of 40 degrees, or more. In some embodiments, beam shaping slit mechanism 120 is shaped such that there is no mechanical interference with specimen positioning system 140 when specimen 101 is oriented at an angle, α, of 60 degrees, or more.

In general, x-ray optics shape and direct x-ray radiation to specimen 101. In some examples, the x-ray optics include an x-ray monochromator to monochromatize the x-ray beam that is incident on the specimen 101. In one example, a crystal monochromator such as a Loxley-Tanner-Bowen monochromator is employed to monochromatize the beam of x-ray radiation. In some examples, the x-ray optics collimate or focus the x-ray beam onto inspection area 102 of specimen 101 to less than 1 milliradian divergence using multilayer x-ray optics. In these examples, the multilayer x-ray optics function as a beam monochromator, also. In some embodiments, the x-ray optics include one or more x-ray collimating mirrors, x-ray apertures, x-ray beam stops, refractive x-ray optics, diffractive optics such as zone plates, Montel optics, specular x-ray optics such as grazing incidence ellipsoidal mirrors, polycapillary optics such as hollow capillary x-ray waveguides, multilayer optics or systems, or any combination thereof. Further details are described in U.S. Patent Publication No. 2015/0110249, the content of which is incorporated herein by reference it its entirety.

X-ray detector 119 collects x-ray radiation 114 scattered from specimen 101 and generates an output signals 135 indicative of properties of specimen 101 that are sensitive to the incident x-ray radiation in accordance with a T-SAXS measurement modality. In some embodiments, scattered x-rays 114 are collected by x-ray detector 119 while specimen positioning system 140 locates and orients specimen 101 to produce angularly resolved scattered x-rays.

In some embodiments, a T-SAXS system includes one or more photon counting detectors with high dynamic range (e.g., greater than $10^5$) and thick, highly absorptive crystal substrates that absorb the direct beam (i.e., zero order beam) without damage and with minimal parasitic backscattering. In some embodiments, a single photon counting detector detects the position and number of detected photons.

In some embodiments, the x-ray detector resolves one or more x-ray photon energies and produces signals for each x-ray energy component indicative of properties of the specimen. In some embodiments, the x-ray detector 119 includes any of a CCD array, a microchannel plate, a photodiode array, a microstrip proportional counter, a gas filled proportional counter, a scintillator, or a fluorescent material.

In this manner the X-ray photon interactions within the detector are discriminated by energy in addition to pixel location and number of counts. In some embodiments, the X-ray photon interactions are discriminated by comparing the energy of the X-ray photon interaction with a predetermined upper threshold value and a predetermined lower threshold value. In one embodiment, this information is communicated to computing system 130 via output signals 135 for further processing and storage.

In a further aspect, a T-SAXS system is employed to determine properties of a specimen (e.g., structural parameter values) based on one or more diffraction orders of scattered light. As depicted in FIG. 1, metrology tool 100 includes a computing system 130 employed to acquire signals 135 generated by detector 119 and determine properties of the specimen based at least in part on the acquired signals.

In some examples, metrology based on T-SAXS involves determining the dimensions of the sample by the inverse solution of a pre-determined measurement model with the measured data. The measurement model includes a few (on the order of ten) adjustable parameters and is representative of the geometry and optical properties of the specimen and the optical properties of the measurement system. The method of inverse solve includes, but is not limited to, model based regression, tomography, machine learning, or any combination thereof. In this manner, target profile parameters are estimated by solving for values of a parameterized measurement model that minimize errors between the measured scattered x-ray intensities and modeled results.

In a further aspect, T-SAXS measurements are performed over a range of angles of incidence that provide sufficient resolution and depth of penetration to characterize high aspect ratio structures through their entire depth.

In some embodiments, it is desirable to perform measurements at different orientations described by rotations about the x and y axes indicated by coordinate system 146 depicted in FIG. 1. This increases the precision and accuracy of measured parameters and reduces correlations among parameters by extending the number and diversity of data sets available for analysis to include a variety of large-angle, out of plane orientations. Measuring specimen parameters with a deeper, more diverse data set also reduces correlations among parameters and improves measurement accuracy. For example, in a normal orientation, T-SAXS is able to resolve the critical dimension of a feature, but is largely insensitive to sidewall angle and height of a feature. However, by collecting measurement data over a broad range of out of plane angular positions, the sidewall angle and height of a feature can be resolved.

Measurements of the intensity of diffracted radiation as a function of x-ray incidence angle relative to the wafer surface normal are collected. Information contained in the multiple diffraction orders is typically unique between each model parameter under consideration. Thus, x-ray scattering yields estimation results for values of parameters of interest with small errors and reduced parameter correlation.

As illustrated in FIG. 1, metrology tool 100 includes a specimen positioning system 140 configured to both align specimen 101 and orient specimen 101 over a large range of angles of incidence with respect the beam axis of the scatterometer. In other words, specimen positioning system 140 is configured to rotate specimen 101 over a large angular range about one or more axes of rotation aligned in-plane with the surface of specimen 101. In some embodiments, specimen positioning system 140 is configured to rotate specimen 101 within a range of at least 120 degrees about one or more axes of rotation aligned in-plane with the surface of specimen 101. In some embodiments, specimen positioning system is configured to rotate specimen 101 within a range of at least 90 degrees about one or more axes of rotation aligned in-plane with the surface of specimen 101. In this manner, angle resolved measurements of specimen 101 are collected by metrology system 100 over any number of locations on the surface of specimen 101. In one example, computing system 130 communicates command signals to motion controller 145 of specimen positioning system 140 that indicate the desired position of specimen 101. In response, motion controller 145 generates command signals to the various actuators of specimen positioning system 140 to achieve the desired positioning of specimen 101.

By way of non-limiting example, as illustrated in FIG. 1, specimen positioning system 140 includes an edge grip chuck 141 to fixedly attach specimen 101 to specimen positioning system 140. A rotational actuator 142 is configured to rotate edge grip chuck 141 and the attached specimen 101 with respect to a perimeter frame 143. In the depicted embodiment, rotational actuator 142 is configured to rotate specimen 101 about the x-axis of the coordinate system 146 illustrated in FIG. 1. As depicted in FIG. 1, a rotation of specimen 101 about the z-axis is an in plane rotation of specimen 101. Rotations about the x-axis and the y-axis (not shown) are out of plane rotations of specimen 101 that effectively tilt the surface of the specimen with respect to the scatterometry elements of metrology system 100. Although it is not illustrated, a second rotational actuator is configured to rotate specimen 101 about the y-axis. A linear actuator 144 is configured to translate perimeter frame 143 in the x-direction. Another linear actuator (not shown) is configured to translate perimeter frame 143 in the y-direction. In this manner, every location on the surface of specimen 101 is available for measurement over a range of out of plane angular positions. For example, in one embodiment, a location of specimen 101 is measured over several angular increments within a range of −45 degrees to +45 degrees with respect to the normal orientation of specimen 101.

In general, specimen positioning system 140 may include any suitable combination of mechanical elements to achieve the desired linear and angular positioning performance, including, but not limited to goniometer stages, hexapod stages, angular stages, and linear stages.

In general, the focal plane of the illumination optics system is optimized for each measurement application. In this manner, system 100 is configured to locate the focal plane at various depths within the specimen depending on the measurement application. In one example, the specimen positioning system 140 is configured to move specimen 101 in the z-direction to locate the wafer within the focal plane of the optical system at the desired depth within specimen 101.

Figure 3:
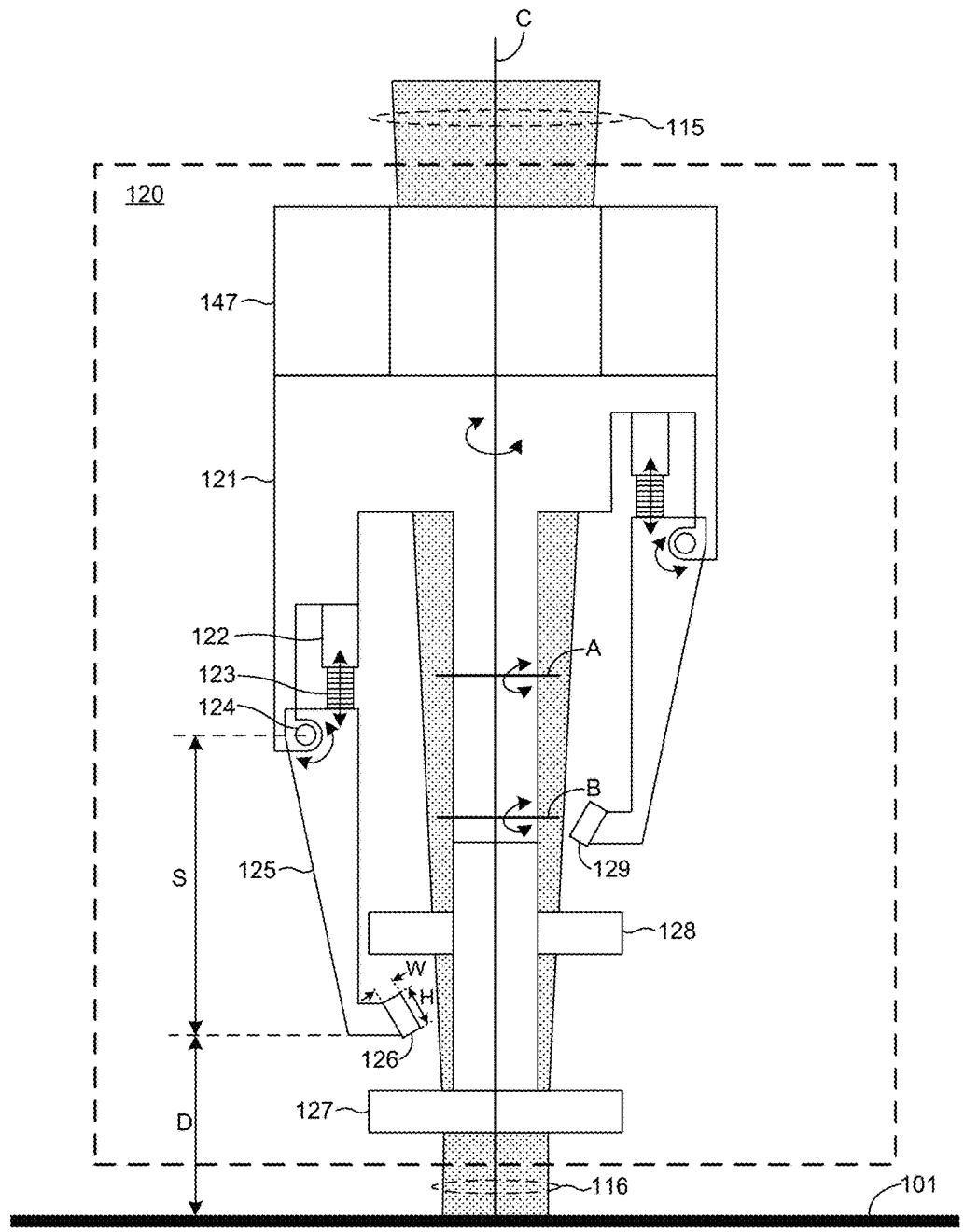
FIG. 3 depicts an embodiment of beam shaping slit mechanism 120 in at least one novel aspect.

FIG. 3 depicts an embodiment of beam shaping slit mechanism 120 in at least one novel aspect. Beam shaping slit mechanism 120 includes multiple, independently actuated beam shaping slits. In the embodiment depicted in FIG. 3, beams shaping slit mechanism 120 includes four independently actuated beam shaping slits 126-129. These four beams shaping slits effectively block a portion of incoming beam 115 and generate an output beam having a box shaped illumination cross-section.

Figure 5:
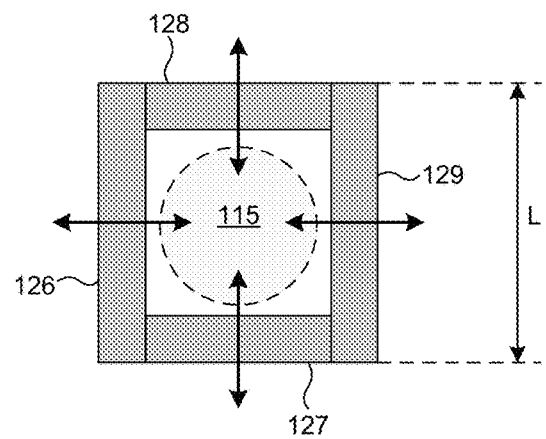
FIG. 5 depicts a top-down view of beam shaping slit mechanism 120 in one configuration.
Figure 6:
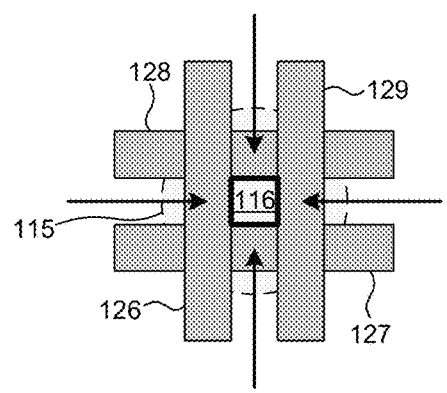
FIG. 6 depicts a top-down view of beam shaping slit mechanism 120 in another configuration.

FIG. 5 depicts a top-down view of beam shaping slit mechanism 120 depicted in FIG. 3. As illustrated in FIGS. 5 and 6, the beam axis is perpendicular to the drawing page. As depicted in FIG. 5, incoming beam 115 has a large cross-section. In some embodiments, incoming beam 115 has a diameter of approximately one millimeter. Furthermore, the location of incoming beam 115 within slits 126-129 may have an uncertainty of approximately three millimeters due to beam pointing errors. To accommodate the size of the incoming beam and the uncertainty of the beam location, each slit has a length, L, of approximately six millimeters. As depicted in FIG. 5, each slit is moveable in a direction perpendicular to the beam axis. In the illustration of FIG. 5, slits 126-129 are located at a maximum distance from the beam axis (i.e., the slits are fully open and they are not restricting the light passing through beam shaping slit mechanism 120.

FIG. 6 depicts slits 126-129 of beam shaping slit mechanism 120 in positions that block a portion of incoming beam 115, such that outgoing beam 116 delivered to the specimen under measurement has reduced size and well-defined shape. As depicted in FIG. 6, each of slits 126-129 has moved inward, toward the beam axis to achieve the desired output beam shape.

As depicted in FIG. 3, by way of example, slit 126 is coupled to a slender pivot arm structure 125. Pivot arm structure 125 pivots about pivot joint 124 causing slit 126 to move in a direction perpendicular to the beam axis as described with reference to FIGS. 5 and 6. An actuator 123 positions pivot arm structure 125 and slit 126 by rotating pivot arm structure 125 and slit 126 about pivot joint 124. In the embodiment depicted in FIG. 3, actuator 123 is a linear, piezoelectric actuator that provides high stiffness positioning capability. In some embodiments, actuator 123 positions slit 126 in a direction perpendicular to the beam axis with a positioning uncertainty of less than ten micrometers. In some embodiments, actuator 123 positions slit 126 in a direction perpendicular to the beam axis with a positioning range of approximately two millimeters, or more. A measurement system 122 precisely measures the position of pivot arm structure 125 and slit 126. In the embodiment depicted in FIG. 3, measurement system 122 is a linear encoder that measures the displacement of actuator 123. In this manner, closed loop position control of pivot arm structure 125 and slit 126 is realized.

In one aspect, slender pivot arm structure 125 locates slit 126 a distance, S, from the pivot joint 124. In some embodiments, S is greater than one hundred millimeters. In some embodiments, S is greater than one hundred fifty millimeters. In another aspect, slender pivot arm structure 125 locates slit 126 a distance from actuator 123 that is greater than distance, S. In this manner, the profile of beam shaping slit mechanism 120 is small near the surface of specimen 101. If the actuators were located close to the surface of specimen 101 (e.g., less than 100 millimeters), the profile of beam shaping slit mechanism 120 would be too large and would interfere with components of specimen positioning system 140, particularly during measurements at large angles of incidence (e.g., a greater than 30 degrees). In some embodiments, the distance, D, between slit 126 and the surface of specimen 101 is less than fifty millimeters. In some embodiments, the distance, D, between slit 126 and the surface of specimen 101 is less than thirty millimeters. In some embodiments, the distance, D, between slit 126 and the surface of specimen 101 is less than ten millimeters.

As depicted in FIG. 3, pivot joint 124 is configured such that pivot arm structure 125 rotates with respect to frame 121, actuator 123 moves pivot arm structure 125 with respect to frame 121, and measurement system 122 measures the position of pivot arm structure 125 with respect to frame 121. Similarly, pivot arm structures associated with slits 127-129 also rotate with respect to frame 121, actuators associated with slits 127-129 move the respective pivot arms structures with respect to frame 121, and measurement systems associated with slits 127-129 move measure the position of the respective pivot arm structures with respect to frame 121. For example, slit 127 and its associated pivot arm structure rotate about axis, B, and slit 128 and its associated pivot arm structure rotate about axis, A.

The specific mechanism depicted in FIG. 3 is provided by way of non-limiting example. In general, any mechanism, and associated actuation and measurement techniques, suitable for locating the beam shaping slits close to the surface of specimen 101 and locating the actuators further away from specimen 101 are contemplated within the scope of this patent document. For example, rather than a pivot joint, a linear joint (e.g., linear bearing structure or flexure mechanism) may be employed to allow slender arm structure 125 and slit 126 to move in a direction perpendicular to the beam axis. In these embodiments, a linear actuator may be configured to move slender arm structure 125 and slit 126 in the direction perpendicular to the beam axis. In another embodiment, a rotary actuator may be employed to rotate slender arm structure 125 and slit 126 about pivot joint 124. In some embodiments, the position of each slit is controlled independently (i.e., an actuator moves each slit independently). In some other embodiments, a single actuator controls the position of more than one slit. In some of these embodiments, a single actuator controls the gap between slits, and another actuator controls the offset position of the slit gap with respect to the specimen under measurement (i.e., the position of all of the slits in a direction perpendicular to the incident x-ray beam).

In some embodiments, each of the actuators of beam shaping slit mechanism 120 is located at least five times further from specimen 101 than any of the beam shaping slits 126-129. In other words, if the distance between each of the beam shaping slits 126-129 in the direction aligned with the beam axis is closer than X, then the distance between each of the actuators and specimen 101 in the direction aligned with the beam axis is at least 5×.

Slits 126-129 are constructed from materials that minimize scattering and effectively block incident radiation. Exemplary materials include single crystal materials such as Germanium, Gallium Arsenide, Indium Phosphide, etc. Typically, the slit material is cleaved along grain boundaries, rather than sawn, to minimize scattering across structural boundaries. In addition, the slit is oriented with respect to the incoming beam such that the interaction between the incoming radiation and the internal structure of the slit material produces a minimum amount of scattering. The crystal material is attached to blades made of high density material (e.g., tungsten) for complete blocking of the x-ray beam on one side of the slit. As depicted in FIG. 3, the each slit has a rectangular cross-section (visible in FIG. 3 for slits 126 and 129) having a height, H, and a width, W. In some embodiments, the width is approximately 0.5 millimeters and the height is approximately 1-2 millimeters. As depicted in FIG. 5, the length, L, of a slit is approximately 6 millimeters.

In a further aspect, each of the slits of beam shaping slit mechanism 120 are located in different distance from the surface of specimen 101 along the beam axis. As illustrated in FIG. 3, each of slits 126-129 is located out of plane with respect to the other. In this manner, slits 126-129 can spatially overlap as viewed along the beam axis without mechanical interference.

In another further aspect, beam shaping slit mechanism 120 is configured to rotate about the beam axis in coordination with the orientation of the specimen to optimize the profile of the incident beam for each angle of incidence, azimuth angle, or both. In this manner, the beam shape is matched to the shape of the metrology target. As depicted in FIG. 3, frame 121 is coupled to rotary actuator 147. Rotary actuator 147 rotates frame 121 and all attached mechanisms, actuators, sensors, and slits about axis C. Axis C is nominally aligned with the beam axis of incoming beam 115. Axis C is a mechanically defined axis, but the beam axis is defined by the beam itself, which is subject to change due to beam pointing errors, fluctuations, etc. In a perfect world, axis C and the beam axis are perfectly aligned, however, in practice, nominal deviations exist. In some embodiments, beam shaping slit mechanism 120 is rotatable about axis C by at least ninety degrees. In some embodiments, beam shaping slit mechanism 120 is rotatable about axis C to any orientation.

In some embodiments, x-ray illumination source 110, focusing optics 111, slits 112 and 113, or any combination thereof, are maintained in the same atmospheric environment as specimen 101 (e.g., gas purge environment). However, in some embodiments, the optical path length between and within any of these elements is long and X-ray scattering in air contributes noise to the image on the detector. Hence in some embodiments, any of x-ray illumination source 110, focusing optics 111, and slits 112 and 113 are maintained in a localized, vacuum environment separated from one another and the specimen (e.g., specimen 101) by vacuum windows.

Similarly, in some embodiments, x-ray detector 119 is maintained in the same atmospheric environment as specimen 101 (e.g., gas purge environment). However, in some embodiments, the distance between specimen 101 and x-ray detector 119 is lengthy and X-ray scattering in air contributes noise to the detected signals. Hence in some embodiments, one or more of the x-ray detectors is maintained in a localized, vacuum environment separated from the specimen (e.g., specimen 101) by a vacuum window.

Figure 7:
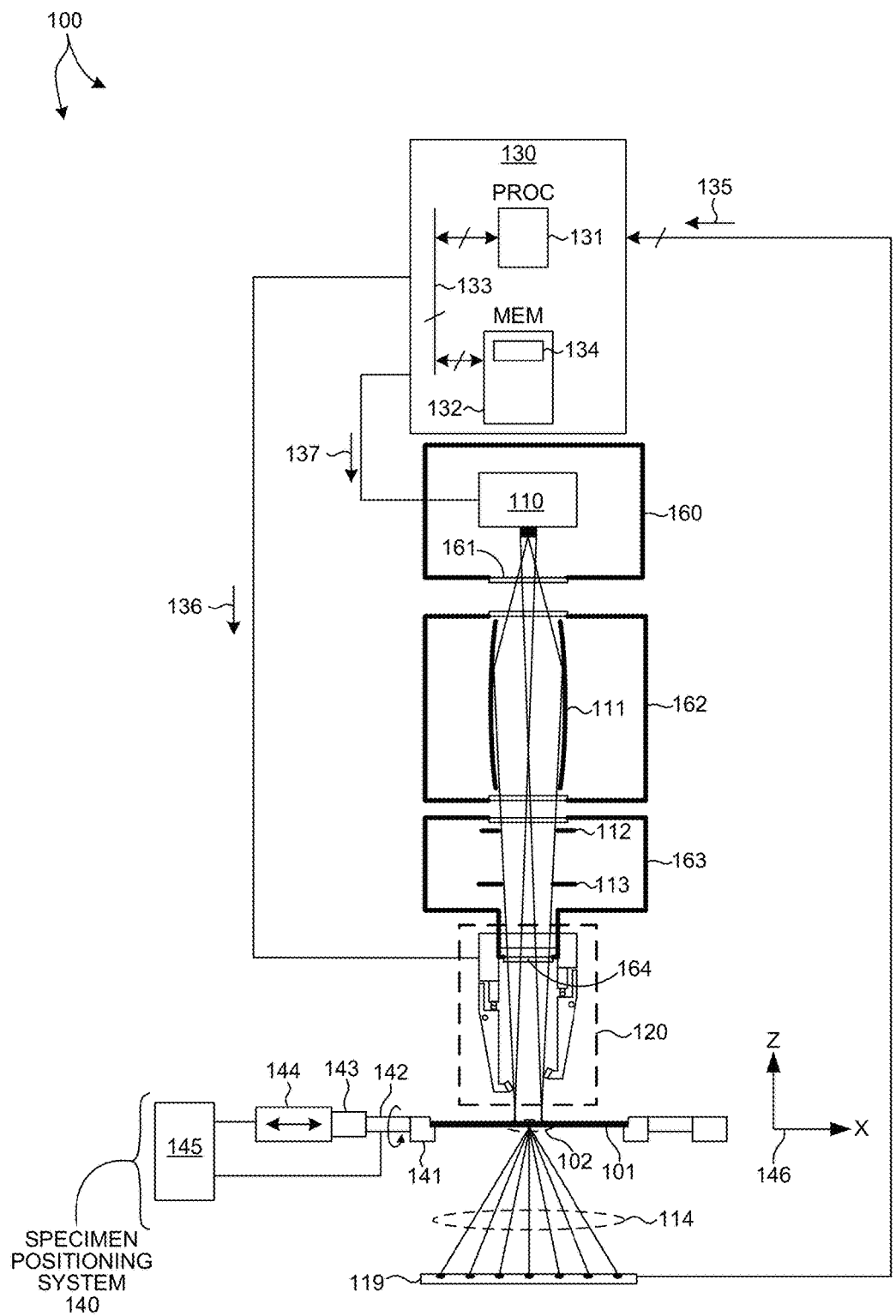
FIG. 7 is a diagram illustrative of elements of metrology system 100 contained in vacuum environments separate from specimen 101.

FIG. 7 is a diagram illustrative of a vacuum chamber 160 containing x-ray illumination source 110, vacuum chamber 162 containing focusing optics 111, and vacuum chamber 163 containing slits 112 and 113. The openings of each vacuum chamber are covered by vacuum windows. For example, the opening of vacuum chamber 160 is covered by vacuum window 161. Similarly, the opening of vacuum chamber 163 is covered by vacuum window 164. The vacuum windows may be constructed of any suitable material that is substantially transparent to x-ray radiation (e.g., Kapton, Beryllium, etc.). A suitable vacuum environment is maintained within each vacuum chamber to minimize scattering of the illumination beam. A suitable vacuum environment may include any suitable level of vacuum, any suitable purged environment including a gas with a small atomic number (e.g., helium), or any combination thereof. In this manner, as much of the beam path as possible is located in vacuum to maximize flux and minimize scattering.

In some embodiments, the entire optical system, including specimen 101, is maintained in vacuum. However, in general, the costs associated with maintaining specimen 101 in vacuum are high due to the complexities associated with the construction of specimen positioning system 140.

In another further aspect, beam shaping slit mechanism 120 is mechanically integrated with vacuum chamber 163 to minimize the beam path length subject to the atmospheric environment. In general, it is desirable to encapsulate as much of the beam as possible in vacuum before incidence with specimen 101. In some embodiments, the vacuum beam line extends into a hollow, cylindrically shaped cavity at the input of beam shaping slit mechanism 120. Vacuum window 164 is located at the output of vacuum chamber 163 within beam shaping slit mechanism 120 such that incoming beam 115 remains in vacuum within a portion of beam shaping slit mechanism 120, then passes through vacuum window 164 before interaction with any of slits 126-129 and specimen 101.

Figure 4:
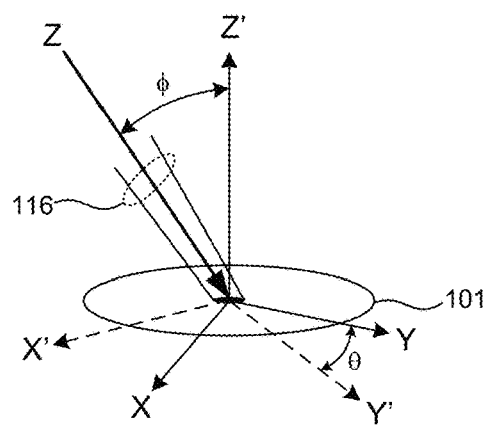
FIG. 4 depicts x-ray illumination beam 116 incident on wafer 101 at a particular orientation described by angles $\phi$ and $\theta$.

As described herein, T-SAXS measurements are performed at multiple orientations of the illuminating x-ray beam relative to the surface normal of the semiconductor wafer. Each orientation is described by any two angular rotations of wafer 101 with respect to the x-ray illumination beam, or vice-versa. In one example, the orientation can be described with respect to a coordinate system fixed to the wafer. FIG. 4 depicts x-ray illumination beam 116 incident on wafer 101 at a particular orientation described by angles $\phi$ and $\theta$. Coordinate frame XYZ is fixed the metrology system and coordinate frame X'Y'Z' is fixed to wafer 101. Y is aligned with an axis in plane with the surface of wafer 101. X and Z are not aligned with the surface of wafer 101. Z' is aligned with an axis normal to the surface of wafer 101, and X' and Y' are in a plane aligned with the surface of wafer 101. As depicted in FIG. 4, x-ray illumination beam 116 is aligned with the Z-axis and thus lies within the XZ plane. Angle, $\phi$, describes the orientation of the x-ray illumination beam 116 with respect to the surface normal of the wafer in the XZ plane. Furthermore, angle, $\theta$, describes the orientation of the XZ plane with respect to the X'Z' plane. Together, $\theta$ and $\phi$, uniquely define the orientation of the x-ray illumination beam 116 with respect to the surface of wafer 101. In this example, the orientation of the x-ray illumination beam with respect to the surface of wafer 101 is described by a rotation about an axis normal to the surface of wafer 101 (i.e., Z' axis) and a rotation about an axis aligned with the surface of wafer 101 (i.e., Y axis). In some other examples, the orientation of the x-ray illumination beam with respect to the surface of wafer 101 is described by a rotation about a first axis aligned with the surface of wafer 101 and another axis aligned with the surface of wafer 101 and perpendicular to the first axis as described with reference to FIG. 1.

In another aspect, the measurement quality and performance of the T-SAXS system is estimated based on properties of the measured zero order beam. The measured properties of the zero order beam include, but are not limited to beam shape, intensity, location, profile, tilt, rotation, asymmetry, or any combination thereof.

In some examples, the total flux of the illumination source is estimated based on a summation of all light detected by the detector. In the absence of external perturbations, the total measured flux depends on target absorption only. In some examples, the measurement is performed without a target.

In some examples, the transmission efficiency of the system is estimated based on a summation of all light detected by the detector. In these examples, light emitted by the illumination source is measured as it exits the illumination source, but before interaction with the illumination optics. In addition, the light detected by the detector is summed. The ratio of flux between the light detected at the detector and the light emitted by the illumination source provides an estimate of the transmission efficiency of the optical system. In some examples, the measurement is performed without a target. In some other examples, a target having known absorption characteristics is employed.

In some examples, the relative alignment of the detector to the beam axis is estimated based on the location of incidence of the zero order beam on the detector.

In some examples, defects or misalignments in the optical subsystem are estimated based on the shape (e.g., asymmetries, roughness, rotations) of the zero order beam measured at the detector. Defects or misalignment of beam shaping optics, slits, apertures, illumination source, etc., may be characterized in this manner. In many examples, errors in the slope of an illumination optic manifest themselves as fine structures of the beam shape detected at the detector. Small variations in the detected beam shape correspond to the position of the beam on the illumination optic. In addition, the position of the beam on the slits is ascertained by monitoring the locations of fine structures due to optic slope errors relative to the location of sharp edges due to the slits.

In a further aspect, the measurement quality and performance of the metrology system is controlled based on the measured zero order beam. In some examples, the estimates of measurement quality and performance described hereinbefore are provided as input to a feedback controller (e.g., computing system 130). The feedback controller communicates control commands that result in changes in state of one or more elements of the metrology system that improves measurement system quality and performance.

In some examples, the control commands are provided to the illumination source. In response, the illumination source is adjusted to change the scanned spot size and shape, illumination power, spot offsets, incident angles, etc. In one example, the parameters of the electron beam incident on the source target are adjusted to change the scanned spot size and shape, illumination power, spot offsets, incident angles, etc.

In some examples, the control commands are provided to one or more positioning devices that control the location of one or more optical elements of the metrology system. In response, the one or more positioning devices changes a position/orientation of one or more optical elements to adjust the incidence angles, focal distance between the illumination source and illumination optics, beam positioning, beam spot size, location of the beam spot on the optic to minimize the effects of surface roughness, etc.

In general, the estimates and control of measurement quality and performance as described herein may be performed with or without a target present in the beam path.

In another further aspect, computing system 130 is configured to generate a structural model (e.g., geometric model, material model, or combined geometric and material model) of a measured structure of a specimen, generate a T-SAXS response model that includes at least one geometric parameter from the structural model, and resolve at least one specimen parameter value by performing a fitting analysis of T-SAXS measurement data with the T-SAXS response model. The analysis engine is used to compare the simulated T-SAXS signals with measured data thereby allowing the determination of geometric as well as material properties such as electron density of the sample. In the embodiment depicted in FIG. 1, computing system 130 is configured as a model building and analysis engine configured to implement model building and analysis functionality as described herein.

Figure 8:
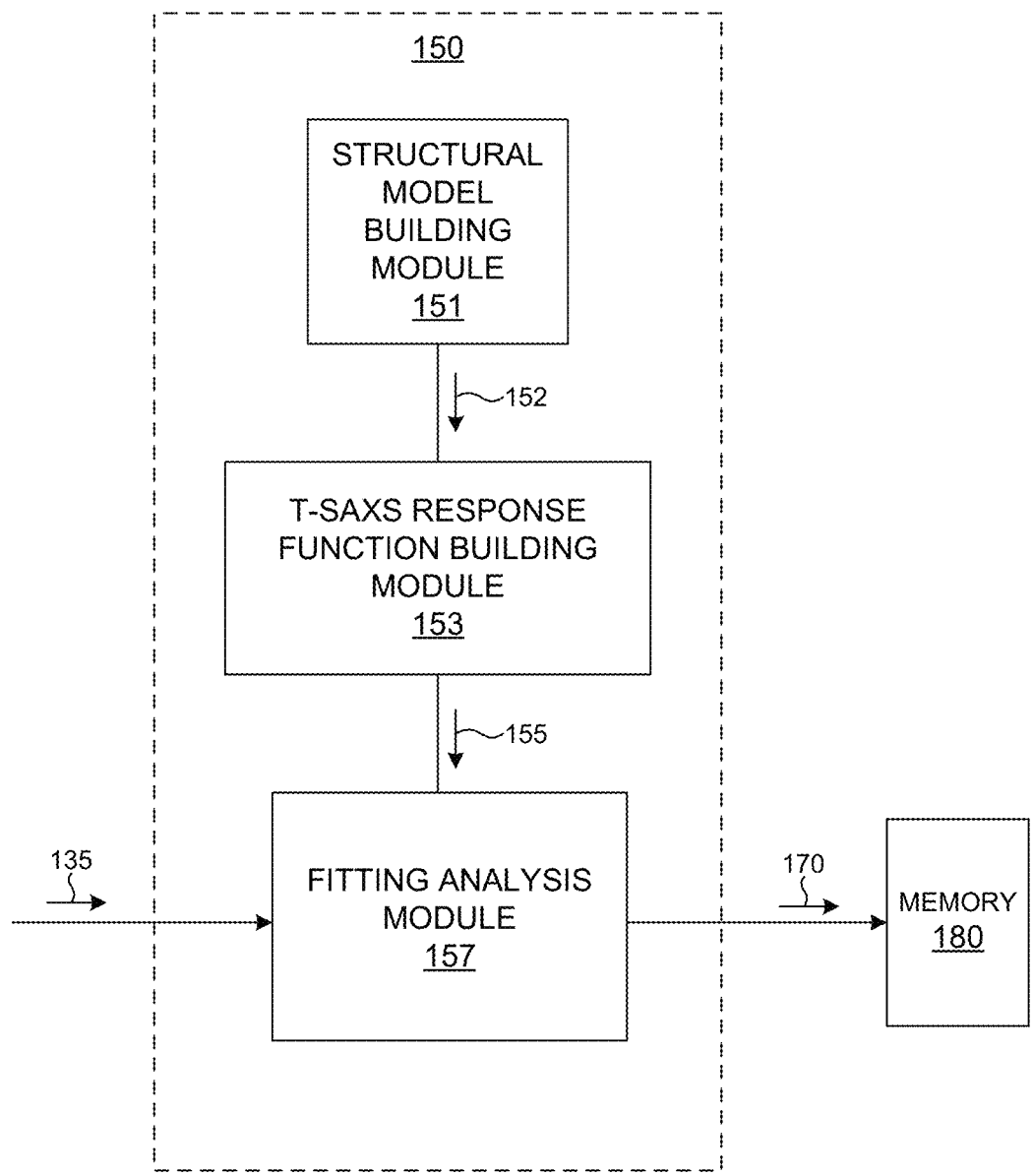
FIG. 8 is a diagram illustrative of a model building and analysis engine 150 configured to resolve specimen parameter values based on T-SAXS data in accordance with the methods described herein.

FIG. 8 is a diagram illustrative of an exemplary model building and analysis engine 150 implemented by computing system 130. As depicted in FIG. 8, model building and analysis engine 150 includes a structural model building module 151 that generates a structural model 152 of a measured structure of a specimen. In some embodiments, structural model 152 also includes material properties of the specimen. The structural model 152 is received as input to T-SAXS response function building module 153. T-SAXS response function building module 153 generates a T-SAXS response function model 155 based at least in part on the structural model 152. In some examples, the T-SAXS response function model 155 is based on x-ray form factors, $$F(\vec{q}) = \int \rho(\vec{r}) e^{-i\vec{q}\cdot\vec{r}} d\vec{r} \quad (2)$$

where F is the form factor, q is the scattering vector, and $\rho(r)$ is the electron density of the specimen in spherical coordinates. The x-ray scattering intensity is then given by $$I(\vec{q}) = F^*F. \quad (3)$$

T-SAXS response function model 155 is received as input to fitting analysis module 157. The fitting analysis module 157 compares the modeled T-SAXS response with the corresponding measured data to determine geometric as well as material properties of the specimen.

In some examples, the fitting of modeled data to experimental data is achieved by minimizing a chi-squared value. For example, for T-SAXS measurements, a chi-squared value can be defined as $$\chi^2_{SAXS} = \frac{1}{N_{SAXS}} \Sigma_j^{N_{SAXS}} \frac{\left(s_j^{SAXS\ model}(v_1, \ldots, v_L) - s_j^{SAXS\ experiment}\right)^2}{\sigma^2_{SAXS,j}} \quad (4)$$

Where, $S_j^{SAXS\ experiment}$ is the measured T-SAXS signals 126 in the "channel" j, where the index j describes a set of system parameters such as diffraction order, energy, angular coordinate, etc. $S_j^{SAXS\ model}(v_1, \ldots, v_L)$ is the modeled T-SAXS signal $S_j$ for the "channel" j, evaluated for a set of structure (target) parameters $v_1, \ldots, v_L$, where these parameters describe geometric (CD, sidewall angle, overlay, etc.) and material (electron density, etc.). $\sigma_{SAXS,j}$ is the uncertainty associated with the jth channel. $N_{SAXS}$ is the total number of channels in the x-ray metrology. L is the number of parameters characterizing the metrology target.

Equation (4) assumes that the uncertainties associated with different channels are uncorrelated. In examples where the uncertainties associated with the different channels are correlated, a covariance between the uncertainties, can be calculated. In these examples a chi-squared value for T-SAXS measurements can be expressed as $$\chi^2_{SAXS} = \frac{1}{N_{SAXS}} \left(\vec{S}_j^{SAXS.\ model}(v_1, \ldots, v_M) - \vec{S}_j^{SAXS.\ experiment}\right)^T \quad (5)$$
$$V_{SAXS}^{-1} \left(\vec{S}_j^{SAXS.\ model}(v_1, \ldots, v_M) - \vec{S}_j^{SAXS.\ experiment}\right)$$

where, $V_{SAXS}$ is the covariance matrix of the SAXS channel uncertainties, and T denotes the transpose.

In some examples, fitting analysis module 157 resolves at least one specimen parameter value by performing a fitting analysis on T-SAXS measurement data 135 with the T-SAXS response model 155. In some examples, $\chi^2_{SAXS}$ is optimized.

As described hereinbefore, the fitting of T-SAXS data is achieved by minimization of chi-squared values. However, in general, the fitting of T-SAXS data may be achieved by other functions.

The fitting of T-SAXS metrology data is advantageous for any type of T-SAXS technology that provides sensitivity to geometric and/or material parameters of interest. Specimen parameters can be deterministic (e.g., CD, SWA, etc.) or statistical (e.g., rms height of sidewall roughness, roughness correlation length, etc.) as long as proper models describing T-SAXS beam interaction with the specimen are used.

In general, computing system 130 is configured to access model parameters in real-time, employing Real Time Critical Dimensioning (RTCD), or it may access libraries of pre-computed models for determining a value of at least one specimen parameter value associated with the specimen 101. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference.

In some examples, model building and analysis engine 150 improves the accuracy of measured parameters by any combination of feed sideways analysis, feed forward analysis, and parallel analysis. Feed sideways analysis refers to taking multiple data sets on different areas of the same specimen and passing common parameters determined from the first dataset onto the second dataset for analysis. Feed forward analysis refers to taking data sets on different specimens and passing common parameters forward to subsequent analyses using a stepwise copy exact parameter feed forward approach. Parallel analysis refers to the parallel or concurrent application of a non-linear fitting methodology to multiple datasets where at least one common parameter is coupled during the fitting.

Multiple tool and structure analysis refers to a feed forward, feed sideways, or parallel analysis based on regression, a look-up table (i.e., "library" matching), or another fitting procedure of multiple datasets. Exemplary methods and systems for multiple tool and structure analysis is described in U.S. Pat. No. 7,478,019, issued on Jan. 13, 2009, to KLA-Tencor Corp., the entirety of which is incorporated herein by reference.

In another further aspect, an initial estimate of values of one or more parameters of interest is determined based on T-SAXS measurements performed at a single orientation of the incident x-ray beam with respect to the measurement target. The initial, estimated values are implemented as the starting values of the parameters of interest for a regression of the measurement model with measurement data collected from T-SAXS measurements at multiple orientations. In this manner, a close estimate of a parameter of interest is determined with a relatively small amount of computational effort, and by implementing this close estimate as the starting point for a regression over a much larger data set, a refined estimate of the parameter of interest is obtained with less overall computational effort.

In another aspect, metrology tool 100 includes a computing system (e.g., computing system 130) configured to implement beam control functionality as described herein. In the embodiment depicted in FIG. 1, computing system 130 is configured as a beam controller operable to control any of the illumination properties such as intensity, divergence, spot size, polarization, spectrum, and positioning of the incident illumination beam 116.

As illustrated in FIG. 1, computing system 130 is communicatively coupled to detector 119. Computing system 130 is configured to receive measurement data 135 from detector 119. In one example, measurement data 135 includes an indication of the measured response of the specimen (i.e., intensities of the diffraction orders). Based on the distribution of the measured response on the surface of detector 119, the location and area of incidence of illumination beam 116 on specimen 101 is determined by computing system 130. In one example, pattern recognition techniques are applied by computing system 130 to determine the location and area of incidence of illumination beam 116 on specimen 101 based on measurement data 135. In some examples, computing system 130 communicates command signals 137 to x-ray illumination source 110 to select the desired illumination wavelength, or redirect the x-ray emission. In some examples, computing system 130 communicates command signals 136 to beam shaping slit mechanism 120 to change the beam spot size such that incident illumination beam 116 arrives at specimen 101 with the desired beam spot size and orientation. In one example, command signals 136 cause rotary actuator 147, depicted in FIG. 3, to rotate beam shaping slit mechanism 120 to a desired orientation with respect to specimen 101. In another example, command signals 136 cause actuators associated with each of slits 126-129 to change position to reshape the incident beam 116 to a desired shape and size. In some other examples, computing system 130 communicates a command signal to wafer positioning system 140 to position and orient specimen 101 such that incident illumination beam 116 arrives at the desired location and angular orientation with respect to specimen 101.

In a further aspect, T-SAXS measurement data is used to generate an image of a measured structure based on the measured intensities of the detected diffraction orders. In some embodiments, a T-SAXS response function model is generalized to describe the scattering from a generic electron density mesh. Matching this model to the measured signals, while constraining the modelled electron densities in this mesh to enforce continuity and sparse edges, provides a three dimensional image of the sample.

Although, geometric, model-based, parametric inversion is preferred for critical dimension (CD) metrology based on T-SAXS measurements, a map of the specimen generated from the same T-SAXS measurement data is useful to identify and correct model errors when the measured specimen deviates from the assumptions of the geometric model.

In some examples, the image is compared to structural characteristics estimated by a geometric, model-based parametric inversion of the same scatterometry measurement data. Discrepancies are used to update the geometric model of the measured structure and improve measurement performance. The ability to converge on an accurate parametric measurement model is particularly important when measuring integrated circuits to control, monitor, and trouble-shoot their manufacturing process.

In some examples, the image is a two dimensional (2-D) map of electron density, absorptivity, complex index of refraction, or a combination of these material characteristics. In some examples, the image is a three dimensional (3-D) map of electron density, absorptivity, complex index of refraction, or a combination of these material characteristics. The map is generated using relatively few physical constraints. In some examples, one or more parameters of interest, such as critical dimension (CD), sidewall angle (SWA), overlay, edge placement error, pitch walk, etc., are estimated directly from the resulting map. In some other examples, the map is useful for debugging the wafer process when the sample geometry or materials deviate outside the range of expected values contemplated by a parametric structural model employed for model-based CD measurement. In one example, the differences between the map and a rendering of the structure predicted by the parametric structural model according to its measured parameters are used to update the parametric structural model and improve its measurement performance. Further details are described in U.S. Patent Publication No. 2015/0300965, the content of which is incorporated herein by reference it its entirety. Additional details are described in U.S. Patent Publication No. 2015/0117610, the content of which is incorporated herein by reference it its entirety.

In a further aspect, model building and analysis engine 150 is employed to generate models for combined x-ray and optical measurement analysis. In some examples, optical simulations are based on, e.g., rigorous coupled-wave analysis (RCWA) where Maxwell's equations are solved to calculate optical signals such as reflectivities for different polarizations, ellipsometric parameters, phase change, etc.

Values of one or more parameters of interest are determined based on a combined fitting analysis of the detected intensities of the x-ray diffraction orders at the plurality of different angles of incidence and detected optical intensities with a combined, geometrically parameterized response model. The optical intensities are measured by an optical metrology tool that may or may not be mechanically integrated with an x-ray metrology system, such as systems 100 depicted in FIG. 1. Further details are described in U.S. Patent Publication No. 2014/0019097 and U.S. Patent Publication No. 2013/0304424, the contents of each are incorporated herein by reference it their entirety.

In general, a metrology target is characterized by an aspect ratio defined as a maximum height dimension (i.e., dimension normal to the wafer surface) divided by a maximum lateral extent dimension (i.e., dimension aligned with the wafer surface) of the metrology target. In some embodiments, the metrology target under measurement has an aspect ratio of at least twenty. In some embodiments, the metrology target has an aspect ratio of at least forty.

It should be recognized that the various steps described throughout the present disclosure may be carried out by a single computer system 130 or, alternatively, a multiple computer system 130. Moreover, different subsystems of the system 100, such as the specimen positioning system 140, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the x-ray illumination source 110, beam shaping slit mechanism 120, and detector 119 in any manner known in the art. For example, the one or more computing systems 130 may be coupled to computing systems associated with the x-ray illumination source 110, beam shaping slit mechanism 120, and detector 119, respectively. In another example, any of the x-ray illumination source 110, beam shaping slit mechanism 120, and detector 119 may be controlled directly by a single computer system coupled to computer system 130.

The computer system 130 may be configured to receive and/or acquire data or information from the subsystems of the system (e.g., x-ray illumination source 110, beam shaping slit mechanism 120, detector 119, and the like) by a transmission medium that may include wireline and/or wireless portions. In this manner, the transmission medium may serve as a data link between the computer system 130 and other subsystems of the system 100.

Computer system 130 of the metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or external systems). For example, the computing system 130 may be configured to receive measurement data (e.g., signals 135) from a storage medium (i.e., memory 132 or 180) via a data link. For instance, spectral results obtained using detector 119 may be stored in a permanent or semi-permanent memory device (e.g., memory 132 or 180). In this regard, the measurement results may be imported from on-board memory or from an external memory system. Moreover, the computer system 130 may send data to other systems via a transmission medium. For instance, specimen parameter values 170 determined by computer system 130 may be stored in a permanent or semi-permanent memory device (e.g., memory 180). In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some embodiments, a scatterometry analysis as described herein is implemented as part of a fabrication process tool. Examples of fabrication process tools include, but are not limited to, lithographic exposure tools, film deposition tools, implant tools, and etch tools. In this manner, the results of a T-SAXS analysis are used to control a fabrication process. In one example, T-SAXS measurement data collected from one or more targets is sent to a fabrication process tool. The T-SAXS measurement data is analyzed as described herein and the results used to adjust the operation of the fabrication process tool.

Scatterometry measurements as described herein may be used to determine characteristics of a variety of semiconductor structures. Exemplary structures include, but are not limited to, FinFETs, low-dimensional structures such as nanowires or graphene, sub 10 nm structures, lithographic structures, through substrate vias (TSVs), memory structures such as DRAM, DRAM 4F2, FLASH, MRAM and high aspect ratio memory structures. Exemplary structural characteristics include, but are not limited to, geometric parameters such as line edge roughness, line width roughness, pore size, pore density, side wall angle, profile, critical dimension, pitch, thickness, overlay, and material parameters such as electron density, composition, grain structure, morphology, stress, strain, and elemental identification. In some embodiments, the metrology target is a periodic structure. In some other embodiments, the metrology target is aperiodic.

In some examples, measurements of critical dimensions, thicknesses, overlay, and material properties of high aspect ratio semiconductor structures including, but not limited to, spin transfer torque random access memory (STT-RAM), three dimensional NAND memory (3D-NAND) or vertical NAND memory (V-NAND), dynamic random access memory (DRAM), three dimensional FLASH memory (3D-

FLASH), resistive random access memory (Re-RAM), and phase change random access memory (PC-RAM) are performed with T-SAXS measurement systems as described herein.

Figure 9:
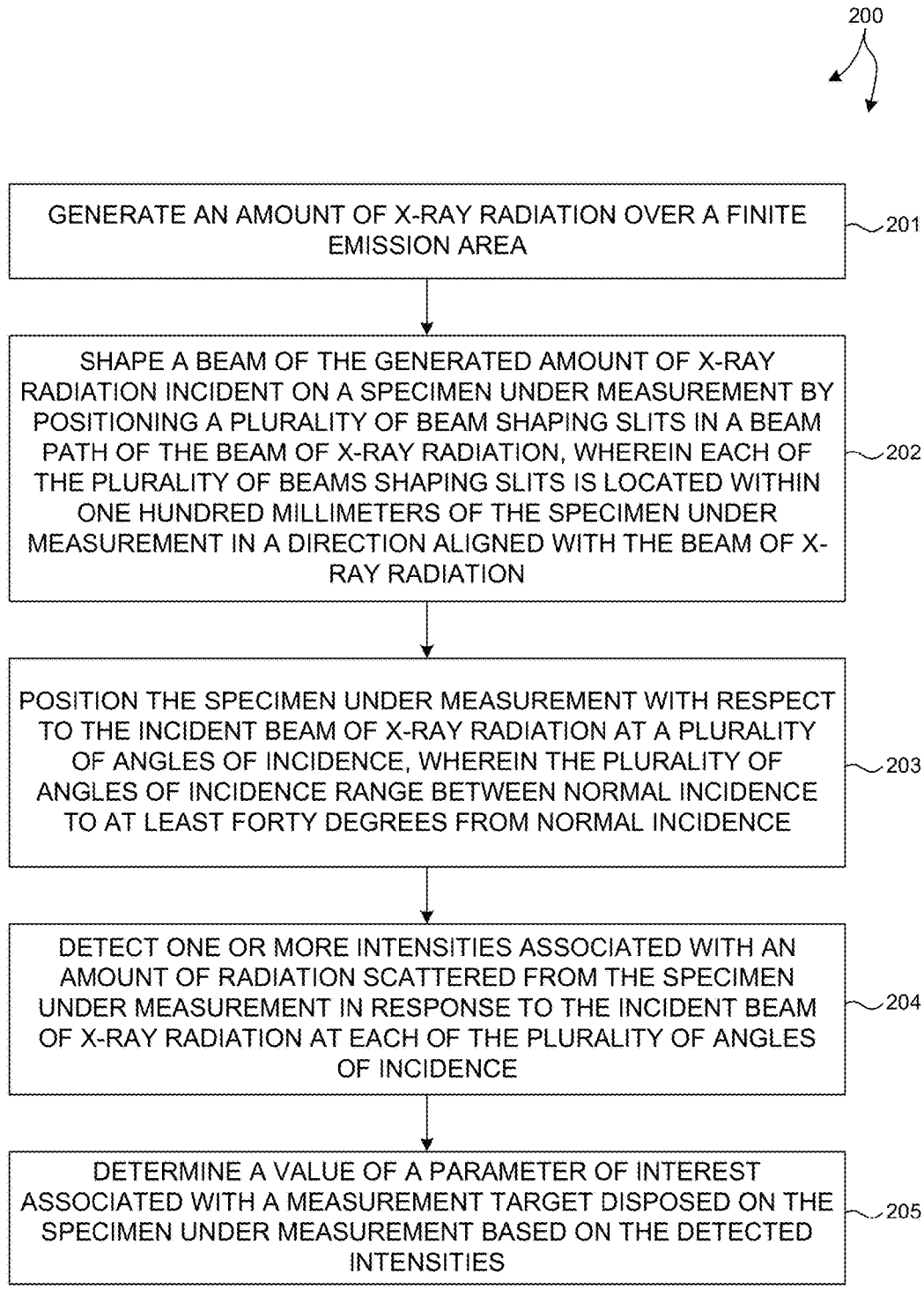
FIG. 9 depicts a flowchart illustrative of an exemplary method 200 of measuring structures based on T-SAXS measurements with beam shaping slits in close proximity to the specimen under measurement as described herein.

FIG. 9 illustrates a method 200 suitable for implementation by the metrology system 100 of the present invention. In one aspect, it is recognized that data processing blocks of method 200 may be carried out via a pre-programmed algorithm executed by one or more processors of computing system 130. While the following description is presented in the context of metrology system 100, it is recognized herein that the particular structural aspects of metrology system 100 do not represent limitations and should be interpreted as illustrative only.

In block 201, an amount of x-ray radiation is generated over a finite emission area.

In block 202, a beam of the generated amount of x-ray radiation incident on a specimen under measurement is shaped by positioning a plurality of beam shaping slits in a beam path of the beam of x-ray radiation. Each of the plurality of beams shaping slits is located within one hundred millimeters of the specimen under measurement in a direction aligned with the beam of x-ray radiation.

In block 203, the specimen under measurement is positioned with respect to the incident beam of x-ray radiation at a plurality of angles of incidence. The plurality of angles of incidence range between normal incidence to at least forty degrees from normal incidence.

In block 204, one or more intensities associated with an amount of radiation scattered from the specimen under measurement are detected in response to the incident beam of x-ray radiation at each of the plurality of angles of incidence.

In block 205, a value of a parameter of interest associated with a measurement target disposed on the specimen under measurement is determined based on the detected intensities.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including critical dimension applications and overlay metrology applications. However, such terms of art do not limit the scope of the term "metrology system" as described herein. In addition, the metrology systems described herein may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the measurement techniques described herein.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, XRF disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
    an x-ray illumination source configured to generate an amount of x-ray radiation, the x-ray illumination source having a finite emission area;
    a beam shaping slit mechanism located in a beam path between the x-ray illumination source and a specimen under measurement, the beam shaping slit mechanism comprising:
        a plurality of beam shaping slits located in close proximity to the specimen;
        a plurality of actuators coupled to a frame of the beam shaping slit mechanism, wherein each of the plurality of actuators is located further from the specimen than any of plurality of beam shaping slits;
        a plurality of arm structures, wherein each arm structure is coupled to one of the plurality of beam shaping slits and one of the actuators; and
        a plurality of measurement systems each configured to measure a displacement of one of the arm structures with respect to the frame, wherein each of the plurality of beam shaping slits blocks a portion of the amount of x-ray radiation to define a beam spot size of x-ray radiation incident on the specimen under measurement;
    an x-ray detector configured to simultaneously detect an intensity associated with an amount of radiation scattered from the specimen under measurement in response to the incident beam of x-ray radiation.

2. The metrology system of claim 1, wherein a distance between each of the plurality of beam shaping slits and the specimen under measurement is less than one hundred millimeters.

3. The metrology system of claim 2, wherein a distance between each of the actuators and the specimen in a direction aligned with the incident beam of x-ray radiation is greater than five times a maximum distance between each of the plurality of beam shaping slits and the specimen in the direction aligned with the incident beam of x-ray radiation.

4. The metrology system of claim 1, further comprising:
    a specimen positioning system configured to position the specimen under measurement with respect to the incident beam of x-ray radiation at a plurality of angles of incidence, wherein the plurality of angles of incidence range between normal incidence to at least twenty degrees from normal incidence.

5. The metrology system of claim 1, further comprising:
    a computing system configured to:
        communicate a command signal to the beam shaping slit mechanism that causes at least one actuator to move at least one beam shaping slit in a direction perpendicular to a beam axis of the incident beam of x-ray radiation.

6. The metrology system of claim 5, wherein the at least one actuator moves the at least one beam shaping slit in a direction perpendicular to a beam axis of the incident beam of x-ray radiation by at least three millimeters with a positioning uncertainty of less than ten micrometers.

7. The metrology system of claim 1, wherein each of the plurality of arm structures is coupled to the frame at a corresponding pivot joint, and wherein the actuator coupled to the arm structure causes the arm structure to rotate about the corresponding pivot joint and move the attached beam shaping slit in a direction perpendicular to the beam axis of the incident beam of x-ray radiation.

8. The metrology system of claim 1, wherein each of the plurality of actuators is a piezoelectric actuator.

9. The metrology system of claim 1, wherein each of the beam shaping slits includes a cleaved, single crystal material.

10. The metrology system of claim 1, wherein a portion of a beam line between the x-ray illumination source and the beam shaping slit mechanism is contained in a vacuum chamber, and wherein a portion of the vacuum chamber is mechanically integrated with the beam shaping slit mechanism.

11. The metrology system of claim 1, the beam shaping slit mechanism, further comprising:
    a rotary actuator coupled to the frame of the beam shaping slit mechanism, wherein the rotary actuator is configured to rotate the beam shaping slit mechanism about an axis nominally aligned with an axis of the beam of x-ray radiation incident on the specimen.

12. The metrology system of claim 1, wherein each of the plurality of beam shaping slits is located at a different distance from the specimen under measurement in a direction aligned with the beam of x-ray radiation incident on the specimen.

13. A beam shaping slit mechanism located in a beam path between an x-ray illumination source and a specimen under measurement, the beam shaping slit mechanism comprising:
    a plurality of beam shaping slits located in close proximity to the specimen;
    a plurality of actuators coupled to a frame of the beam shaping slit mechanism, wherein each of the plurality of actuators is located further from the specimen than any of plurality of beam shaping slits;
    a plurality of arm structures, wherein each arm structure is coupled to one of the plurality of beam shaping slits and one of the actuators; and
    a plurality of measurement systems each configured to measure a displacement of one of the arm structures with respect to the frame, wherein each of the plurality of beam shaping slits blocks a portion of the amount of x-ray radiation to define a beam spot size of x-ray radiation incident on the specimen under measurement.

14. The beam shaping slit mechanism of claim 13, wherein a distance between each of the plurality of beam shaping slits and the specimen under measurement is less than fifty millimeters.

15. The beam shaping slit mechanism of claim 13, wherein a distance between each of the actuators and the specimen in a direction aligned with the incident beam of x-ray radiation is greater than five times a maximum distance between each of the plurality of beam shaping slits and the specimen in the direction aligned with the incident beam of x-ray radiation.

16. The beam shaping slit mechanism of claim 13, further comprising:
    a computing system configured to:
        communicate a command signal to the beam shaping slit mechanism that causes at least one actuator to move at least one beam shaping slit in a direction perpendicular to a beam axis of the incident beam of x-ray radiation.

17. The beam shaping slit mechanism of claim 13, further comprising:

a rotary actuator coupled to the frame of the beam shaping slit mechanism, wherein the rotary actuator is configured to rotate the beam shaping slit mechanism about an axis nominally aligned with an axis of the beam of x-ray radiation incident on the specimen.

18. A method comprising:

generating an amount of x-ray radiation over a finite emission area;

shaping a beam of the generated amount of x-ray radiation incident on a specimen under measurement by positioning a plurality of beam shaping slits in a beam path of the beam of x-ray radiation, wherein each of the plurality of beams shaping slits is located within one hundred millimeters of the specimen under measurement in a direction aligned with the beam of x-ray radiation;

positioning the specimen under measurement with respect to the incident beam of x-ray radiation at a plurality of angles of incidence, wherein the plurality of angles of incidence range between normal incidence to at least forty degrees from normal incidence;

detecting one or more intensities associated with an amount of radiation scattered from the specimen under measurement in response to the incident beam of x-ray radiation at each of the plurality of angles of incidence; and determining a value of a parameter of interest associated with a measurement target disposed on the specimen under measurement based on the detected intensities.

19. The method of claim 18, wherein the positioning of the plurality of beam shaping slits involves communicating a command signal that causes at least one actuator to move at least one of the beam shaping slits in a direction perpendicular to the direction aligned with the beam of x-ray radiation.

20. The method of claim 18, further comprising:

rotating the plurality of beam shaping slits about an axis nominally aligned with an axis of the beam of x-ray radiation incident on the specimen.

* * * * *